US005853388A

United States Patent [19]

Semel

[11] Patent Number: 5,853,388

[45] Date of Patent: Dec. 29, 1998

[54] INTRAVENOUS BAG WITH SEPARATE COMPARTMENT

[76] Inventor: David Semel, 611 N. Vista Del Sol, Mesa, Ariz. 85207

[21] Appl. No.: 915,744

[22] Filed: Aug. 21, 1997

[51] Int. Cl.[6] .................................................... A61M 37/00

[52] U.S. Cl. .............................. 604/82; 604/89; 604/410; 604/416; 141/9; 206/219; 222/97

[58] Field of Search .............................. 604/82, 410, 408, 604/416, 403, 89, 90.91, 92.06; 141/9, 100, 114; 206/219; 222/92, 94, 96, 97

[56] References Cited

U.S. PATENT DOCUMENTS 2,764,983 10/1956 Barasch et al. .......................... 604/416
5,383,579 1/1995 Lanfranconi et al. ................ 604/89 X
5,472,422 12/1995 Ljungquist ............................ 604/82 X
5,560,403 10/1996 Balteau et al. ...................... 604/410 X

*Primary Examiner*—Wynn Wood Coggins
*Assistant Examiner*—N. Kent Gring

[57] ABSTRACT

A new intravenous bag with separate compartments for separating medications and intravenous solutions prior to mixing. The inventive device includes a pouch having an upper section and a lower section. The lower section has an outlet tube extending downwardly therefrom. The outlet tube is in fluid communication with the lower section. A divider wall separates the upper section from the lower section. The divider wall extends between opposing side walls of the pouch and tapers inwardly to a flexible central channel. The flexible central channel has an open upper end within the upper section and an open lower end within the lower section. A seal is disposed within the flexible central channel.

7 Claims, 2 Drawing Sheets

INTRAVENOUS BAG WITH SEPARATE COMPARTMENT

BACKGROUND OF THE INVENTION

1. Field of the Invention

The present invention relates to multiple chamber containers and more particularly pertains to a new intravenous bag with separate compartments for separating medications and intravenous solutions prior to mixing.

2. Description of the Prior Art

The use of multiple chamber containers is known in the prior art. More specifically, multiple chamber containers heretofore devised and utilized are known to consist basically of familiar, expected and obvious structural configurations, notwithstanding the myriad of designs encompassed by the crowded prior art which have been developed for the fulfillment of countless objectives and requirements.

Known prior art multiple chamber containers include U.S. Pat. No. 5,257,985 to Puhl; U.S. Pat. No. 5,431,496 to Balteau et al.; U.S. Pat. No. Des. 346,737 to Dufresne; U.S. Pat. No. 4,997,083 to Loretti et al.; U.S. Pat. No. 4,608,043 to Larkin; and U.S. Pat. No. 4,484,920.

While these devices fulfill their respective, particular objectives and requirements, the aforementioned patents do not disclose a new intravenous bag with separate compartments. The inventive device includes a pouch having an upper section and a lower section. The lower section has an outlet tube extending downwardly therefrom. The outlet tube is in fluid communication with the lower section. A divider wall separates the upper section from the lower section. The divider wall extends between opposing side walls of the pouch and tapers inwardly to a flexible central channel. The flexible central channel has an open upper end within the upper section and an open lower end within the lower section. A seal is disposed within the flexible central channel.

In these respects, the intravenous bag with separate compartments according to the present invention substantially departs from the conventional concepts and designs of the prior art, and in so doing provides an apparatus primarily developed for the purpose of separating medications and intravenous solutions prior to mixing.

SUMMARY OF THE INVENTION

In view of the foregoing disadvantages inherent in the known types of multiple chamber containers now present in the prior art, the present invention provides a new intravenous bag with separate compartments construction wherein the same can be utilized for separating medications and intravenous solutions prior to mixing.

The general purpose of the present invention, which will be described subsequently in greater detail, is to provide a new intravenous bag with separate compartments apparatus and method which has many of the advantages of the multiple chamber containers mentioned heretofore and many novel features that result in a new intravenous bag with separate compartments which is not anticipated, rendered obvious, suggested, or even implied by any of the prior art multiple chamber containers, either alone or in any combination thereof.

To attain this, the present invention generally comprises a pouch having an upper section and a lower section. The upper section has a tab extending upwardly from an upper end thereof. The tab has an aperture therethrough. The lower section has an outlet tube extending downwardly therefrom. The outlet tube is in fluid communication with the lower section. The upper section has medication disposed therein. The lower section has intravenous solution disposed therein. A divider wall separates the upper section from the lower section. The divider wall extends between opposing side walls of the pouch and tapers inwardly to a flexible central channel. The flexible central channel has an open upper end within the upper section and an open lower end within the lower section. A breakable seal is disposed within the flexible central channel intermediate the open upper end and the open lower end thereof. The breakable seal precludes mixing of the medication with the intravenous solution.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature an essence of the technical disclosure of the application. The abstract is neither intended to define the invention of the application, which is measured by the claims, nor is it intended to be limiting as to the scope of the invention in any way.

It is therefore an object of the present invention to provide a new intravenous bag with separate compartments apparatus and method which has many of the advantages of the multiple chamber containers mentioned heretofore and many novel features that result in a new intravenous bag with separate compartments which is not anticipated, rendered obvious, suggested, or even implied by any of the prior art multiple chamber containers, either alone or in any combination thereof.

It is another object of the present invention to provide a new intravenous bag with separate compartments which may be easily and efficiently manufactured and marketed.

It is a further object of the present invention to provide a new intravenous bag with separate compartments which is of a durable and reliable construction.

An even further object of the present invention is to provide a new intravenous bag with separate compartments which is susceptible of a low cost of manufacture with regard to both materials and labor, and which accordingly is then susceptible of low prices of sale to the consuming public, thereby making such intravenous bag with separate compartments economically available to the buying public.

Still yet another object of the present invention is to provide a new intravenous bag with separate compartments which provides in the apparatuses and methods of the prior art some of the advantages thereof, while simultaneously overcoming some of the disadvantages normally associated therewith.

Still another object of the present invention is to provide a new intravenous bag with separate compartments for separating medications and intravenous solutions prior to mixing.

Yet another object of the present invention is to provide a new intravenous bag with separate compartments which includes a pouch having an upper section and a lower section. The lower section has an outlet tube extending downwardly therefrom. The outlet tube is in fluid communication with the lower section. A divider wall separates the upper section from the lower section. The divider wall extends between opposing side walls of the pouch and tapers inwardly to a flexible central channel. The flexible central channel has an open upper end within the upper section and an open lower end within the lower section. A seal is disposed within the flexible central channel.

Still yet another object of the present invention is to provide a new intravenous bag with separate compartments that keeps medication separate from intravenous solution until ready to use in one container.

Even still another object of the present invention is to provide a new intravenous bag with separate compartments that eliminates the need to manually mix medications with intravenous solutions prior to administering.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
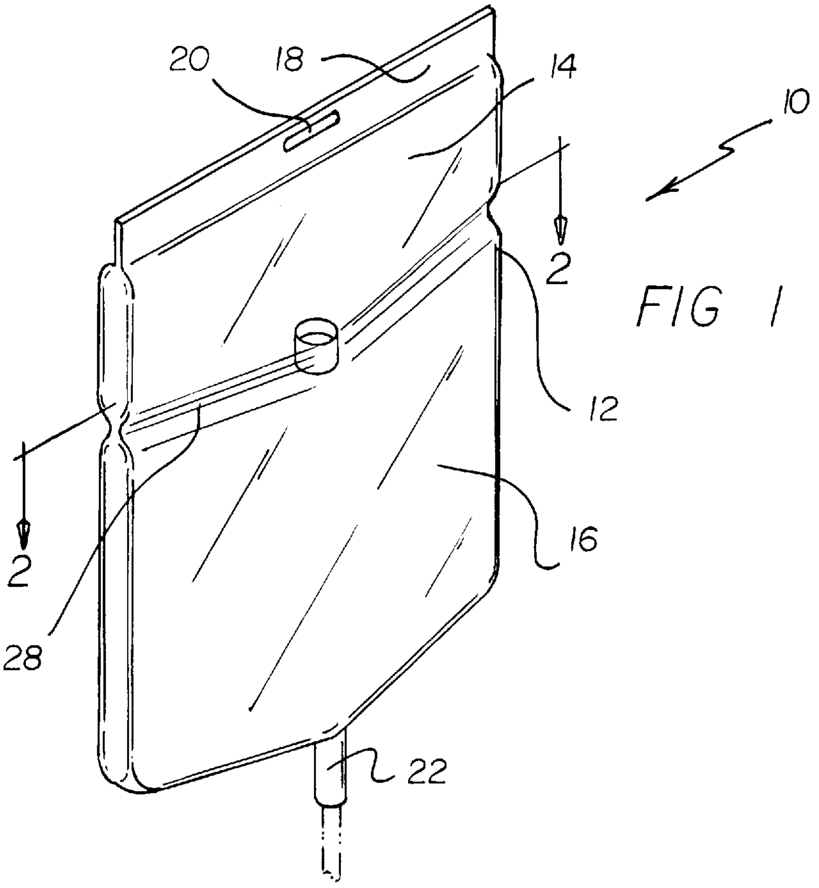
FIG. 1 is a perspective view of a new intravenous bag with separate compartments according to the present invention.
Figure 2:
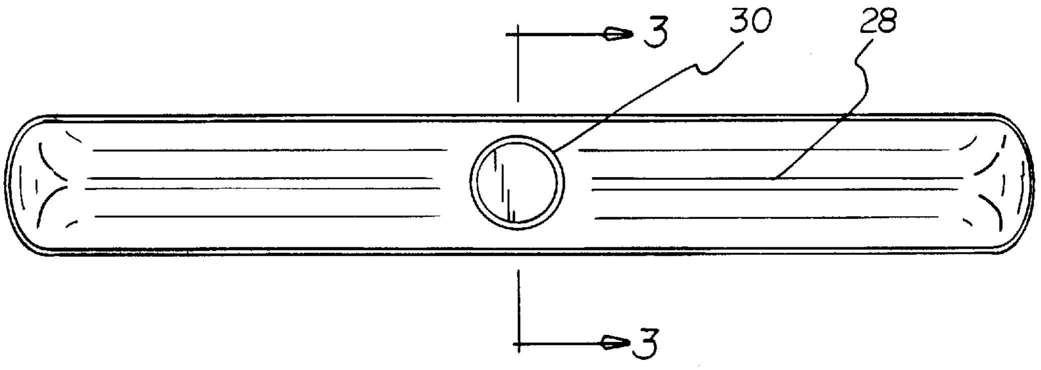
FIG. 2 is a cross-sectional view of the present invention as taken along line 2—2 of FIG. 1.
Figure 3:
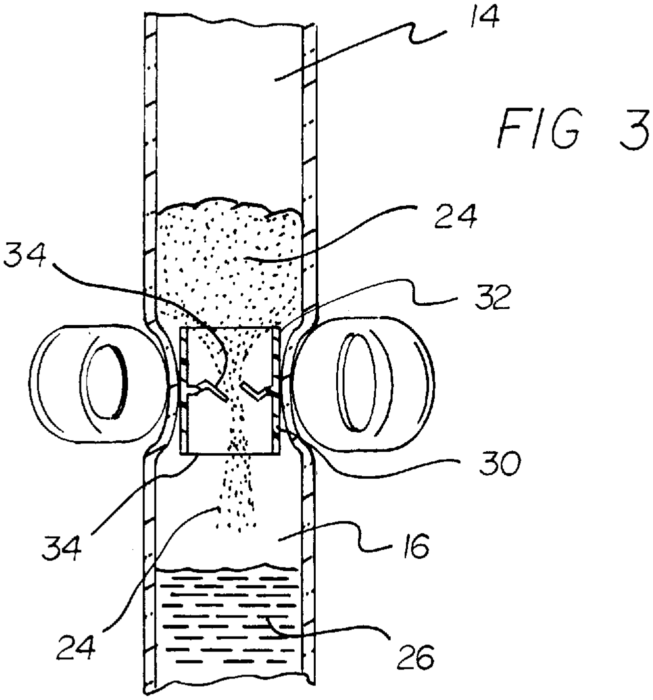
FIG. 3 is a cross-sectional view of the present invention as taken along line 3—3 of FIG. 2.

With reference now to the drawings, and in particular to FIGS. 1 through 4 thereof, a new intravenous bag with separate compartments embodying the principles and concepts of the present invention and generally designated by the reference numeral 10 will be described.

As best illustrated in FIGS. 1 through 4, the intravenous bag with separate compartments 10 comprises a pouch 12 having an upper section 14 and a lower section 16. The upper section 14 has a tab 18 extending upwardly from an upper end thereof. The tab 18 has an aperture 20 therethrough. The aperture 20 allows the pouch 12 to be secured to and hang from a standard intravenous pole. The lower section 16 has an outlet tube 22 extending downwardly therefrom. The outlet tube 22 is in fluid communication with the lower section 16. The upper section 14 has medication 24 disposed therein. The medication 24 is either in powder or liquid form. The lower section 16 has intravenous solution 26 disposed therein. The type of intravenous solution 26 would vary depending upon the type of medication 24 contained within the upper section 14.

A divider wall 28 separates the upper section 14 from the lower section 16. The divider wall 28 extends between opposing side walls of the pouch 12 and tapers inwardly to a flexible central channel 30. The flexible central channel 30 has an open upper end 32 within the upper section 14 and an open lower end 32 within the lower section 16. The tapering of the divider wall 28 allows the medication 24 to gather towards and funnel through the flexible central channel 30.

A breakable seal 34 is disposed within the flexible central channel 30 intermediate the open upper end 32 and the open lower end 34 thereof. The breakable seal 34 precludes mixing of the medication 24 with the intravenous solution 26. An individual simply squeezes inwardly against the flexible central channel 30 to cause the seal 34 to break thereby allowing the medication 24 to funnel through the central channel 30 and mix with the intravenous solution 26 in the lower section 16 prior to being administered to a receiving patient. Note FIG. 3.

Figure 4:
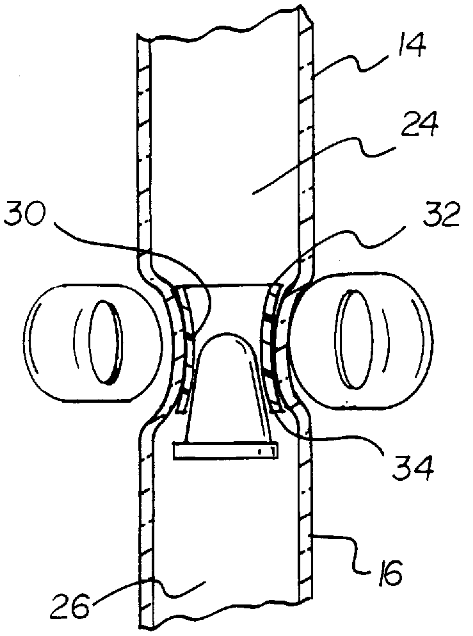
FIG. 4 is a cross-sectional view of an alternate embodiment of the present invention.

In the alternate embodiment, as illustrated in FIG. 4, the breakable seal 34 is replaced with a conical stopper 36 that extends upwardly within the open lower end 34 of the central channel 30. In use, the individual would squeeze inwardly against the flexible central channel 30 thereby causing the stopper 36 to be pushed outwardly and fall within the lower section 16 thereby allowing the medication 24 to funnel through the central channel 30 and mix with the intravenous solution 26 in the lower section prior to being administered to a receiving patient.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An intravenous bag with separate compartments for separating medications and intravenous solutions prior to use comprising, in combination:

a pouch having an upper section and a lower section, the upper section having a tab extending upwardly from an upper end thereof, the tab having an aperture therethrough for suspending the pouch from a support, the lower section having a single outlet tube extending downwardly from a central portion thereof, the outlet tube being in fluid communication with the lower section, the upper section having medication disposed therein, the lower section having intravenous solution disposed therein;

a divider wall separating the upper section from the lower section such that the upper section is positioned entirely above the lower section and the lower section is positioned entirely under the upper section for facilitating complete transfer of the medication from the upper section to the lower section, the divider wall extending between opposing side walls of the pouch and sloping downwardly to a nadir in a middle of the divider wall, a flexible central channel being positioned at the nadir of the divider wall, the flexible central channel having an open upper end within the upper section and an open lower end within the lower section, whereby the sloping divider wall guides the medication to the central channel without tilting of the pouch; and a breakable seal disposed within the flexible central channel intermediate the open upper end and the open lower end thereof, the breakable seal precluding movement of the medication in the upper section into the lower section to mix with the intravenous solution, wherein the breakable seal comprises a thin wall of breakable material extending across the lumen of the central channel to block the channel the thin wall being breakable by application of force to the wall at the edge thereof.

2. An intravenous bag with separate compartments for separating medications and intravenous solutions prior to use comprising, in combination:

a pouch having an upper section and a lower section, the lower section having an outlet tube extending downwardly therefrom, the outlet tube being in fluid communication with the lower section;

a divider wall separating the upper section from the lower section, the divider wall extending between opposing side walls of the pouch and tapering inwardly to a nadir in a middle of the divider wall, a flexible central channel being positioned at the nadir of the divider wall, the flexible central channel having an open upper end within the upper section and an open lower end within the lower section; and sealing means disposed within the flexible central channel.

3. The intravenous bag with separate compartments as set forth in claim 2 wherein the sealing means comprises a breakable seal intermediate the open upper end and the open lower end of the flexible central channel.

4. The intravenous bag with separate compartments as set forth in claim 2 wherein the sealing means comprises a conical stopper extending upwardly through the open lower end of the flexible central channel, said stopper being positioned such that the entire stopper is removable from the channel by a pinching force applied to the central channel urging opposite sides of the channel together, whereby the stopper is forced out of the central channel and into the lower section.

5. An intravenous bag with separate compartments for separating medications and intravenous solutions prior to use comprising, in combination:

a substantially rectangular pouch having an upper section and a lower section, the upper section having an interior volume less than an interior volume of the lower section, the lower section having a lower edge tapering downwardly to an outlet tube extending downwardly from a middle of the lower section, the outlet tube being in fluid communication with the lower section;

a divider wall separating the upper section from the lower section such that the upper section is positioned entirely above the lower section and the lower section is positioned entirely below the upper section for facilitating complete transfer of a substance in said upper section to said lower section, the divider wall extending between opposing side walls of the pouch and tapering inwardly to a nadir in a middle of the divider wall, a flexible central channel having an open upper end within the upper section and an open lower end within the lower section, the flexible central channel being positioned at the nadir of the divider wall such that a substance in the upper section drains completely into the lower section when the channel is open;

sealing means disposed within the flexible central channel such that the channel is closed until the sealing means is opened by a user.

6. The intravenous bag with separate compartments as set forth in claim 5 wherein the sealing means comprises a breakable seal intermediate the open upper end and the open lower end of the flexible central channel.

7. The intravenous bag with separate compartments as set forth in claim 5 wherein the sealing means comprises a conical stopper extending upwardly through the open lower end of the flexible central channel, said stopper being positioned such that the entire stopper is removable from the channel by a force urging opposite sides of the channel together, whereby the stopper is released into the lower section.

* * * * *